United States Patent [19]

Nogami et al.

[11] Patent Number: 4,465,771
[45] Date of Patent: Aug. 14, 1984

[54] PRODUCTION OF ENDURACIDIN AND MICROORGANISMS THEREFOR

[75] Inventors: Ikuo Nogami; Hideo Shirafuji, both of Nagaokakyo; Shigeo Matsumura, Suita, all of Japan

[73] Assignee: Takeda Chemical Industries, Ltd., Osaka, Japan

[21] Appl. No.: 316,901

[22] Filed: Oct. 30, 1981

[30] Foreign Application Priority Data

Oct. 31, 1980 [JP] Japan ................................ 55-154393

[51] Int. Cl.³ ...................... C12P 21/00; C12N 15/00; C12N 1/20; C12R 1/465
[52] U.S. Cl. .................................... 435/68; 435/172.1; 435/253; 435/886; 935/60
[58] Field of Search ................ 435/68, 172, 253, 886, 435/70

[56] References Cited

U.S. PATENT DOCUMENTS 3,697,647 11/1972 Matsuoka et al. .................... 435/68
3,786,142 1/1974 Shibata et al. ...................... 435/886

OTHER PUBLICATIONS

Asai et al., J. Antibiotics, 21(2) 138–146 (1968).
E. Higashide et al., The Journal of Antibiotics, 21, 126 (1968).
K. Mizuno et al., Antimicrobial Agents and Chemotherapy, 6 (1980).
Central Patent Index, Basic Abstract Journal Section B: 42389R–BCD/R 24.
H. Hagino et al., Agri. Biol. Chem., 37 (9) 2013 (1973).

Primary Examiner—Esther M. Kepplinger
Attorney, Agent, or Firm—Wenderoth, Lind & Ponack

[57] ABSTRACT

Enduracidin is produced by cultivating an enduracidin-producing microorganism, which belongs to the genus Streptomyces and which has enduracidin-excreting ability or m-fluoro-DL-tyrosine-resistance or has these two properties, until enduracidin is substantially accumulated in the culture broth, and then recovering the same.

12 Claims, No Drawings

PRODUCTION OF ENDURACIDIN AND MICROORGANISMS THEREFOR

This invention relates to production of enduracidin. More particularly, this invention provides a method of producing enduracidin which comprises cultivating an enduracidin-producing microorganism, which belongs to the genus Streptomyces and which has enduracidin-excreting ability of m-fluoro-DL-tyrosine-resistance or has these two properties, until enduracidin is substantially accumulated in the culture broth, and then recovering the same. This invention further provides novel enduracidin-producing microorganisms belonging to the genus Strepromyces or their biologically pure cultures, which have the above-mentioned properties.

The antibiotic enduracidin (=enramycin) has a broad antibacterial spectrum against gram-positive bacteria and is a useful polypeptide-type antibiotic substance as, among others, an additive to feedstuff.

Enduracidin is the generic name of enduracidin analogs and includes enduracidin A, B, C and D. Among them, enduracidin A and B are main components of enduracidin produced by microorganisms, and their chemical structures have been well established [Antimicrobial Agents and Chemotherapy, 6(1970); Central Patent Index, Basic Abstract Journal Section B: 42389R-BCD/R24=Japanese Patent Publication 7017158].

As a method of producing enduracidin, there has been known the one in which *Streptomyces fungicidicus* B-5477 (IFO-12439, ATCC-21013) and *Streptomyces fungicidus* B-5477-m (IFO-12440, ATCC-21014) are employed [U.S. Pat. No. 3,786,142; Journal of Antibiotics, 21, 126 (1968)].

The present inventors conducted extensive study with the purpose of obtaining more efficient enduracidin-producing microorganisms, and found that an enduracidin-producing microorganism, which has enduracidin-excreting ability or m-fluoro-DL-tyrosine-resistance or has these two properties, is capable of producing several times as much yield of enduracidin as the parent strain does.

Concrete explanation of the microorganisms employable in this invention will be given as follows:

A substantial amount of the enduracidin produced by known enduracidin-producing strains is usually accumulated intracellularly, whether the culture medium may be liquid or solid.

The enduracidin-excreting microorganisms mentioned herein are those which have come to excrete or permeably diffuse enduracidin around the colonies on solid medium under the conditions that the colonies of the parent strains do not excrete or permeably diffuse enduracidin extracellularly.

The enduracidin-excreting mutants can be obtained, for example, by spreading the spores or fragments of mycelia processed by conventional means for causing mutation such as ultra-violet ray irradiation, treating with N-methyl-N'-nitro-N-nitrosoguanidine or X-ray irradiation on bouillon-agar plates to cause ten to several tens colonies to be formed per plate (9 cm). When the colonies have grown sufficiently, i.e., after 4-6 day cultivation at 28° C., soft agar containing the spores of the test organism *Bacillus subtilis* PCI 219 is layered on each plate.

Thus-layered plates are incubated at 37° C. for 16 hours, then the colonies forming the growth-inhibitory zone of the test organisms around them are found, thus the enduracidin-excreting mutants are obtained. The mutants appear at the frequency of one to three among ten thousand colonies subjected to ultra-violet ray irradiation. Thus obtained enduracidin-excreting microorganisms have a higher productivity of enduracidin as compared with parent strains. Especially on an inorganic phosphate-supplemented medium, the productivity of enduracidin by the microorganism reaches about twice as much as the parent strains. *Streptomyces fungicidicus* GAB-453 strain (IFO-14036; FERM P-5728; ATCC-31729) is an example of those employable advantageously.

On the other hand, m-fluoro-DL-tyrosine resistant microorganisms can be obtained by the following procedure.

The parent strain B-5477 cannot grow on a minimal agar plate medium supplemented with m-fluoro-DL-tyrosine at the concentration of 3 γ/ml or higher, the said medium consisting of glucose 1.0%, ammonium sulfate 0.2%, potassium dihydrogen phosphate 0.1%, sodium chloride 0.1%, magnesium sulfate 0.1%, calcium carbonate 0.2%, ferrous sulfate 1 ppm, manganese chloride 1 ppm, zinc sulfate 1 ppm, and agar 2.0%. Therefore, microorganisms which have come to be capable of growing on the said minimal agar plate medium containing m-fluoro-DL-tyrosine at the concentration of 3 γ/ml or higher by spontaneous mutation of the parent strains or by causing mutation of the parent strains by a conventional mutagenic treatment are called m-fluoro-DL-tyrosine-resistant mutants. As the microorganisms producing enduracidin in high potency, those which are capable of growing sufficiently on a minimal agar medium containing m-fluoro-DL-tyrosine at a concentration of 60 γ-200 γ/ml are usually preferable. Such microorganisms can be obtained by inoculating a minimal agar medium containing 60-200 γ/ml of m-fluoro-DL-tyrosine with the spore-suspension of the parent strains with or without mutagenic treatment, then incubating the inoculated medium at 28° C. for 5-7 days, and isolating the colonies.

As the mutagens, there may be counted, besides the ultra-violet ray, conventional ones such as N-methyl-N'-nitro-N-nitrosoguanidine, methylmethanesulfonic acid or X-ray.

Frequency of obtaining m-fluoro-DL-tyrosine resistant strains usually ranges 0.00001-0.0001 percent. Enduracidin-productivity of most of thus obtained m-fluoro-DL-tyrosine resistant strains is about two times as high as that of the parent strain. Among these obtained strains, *Streptomyces fungicidicus* Emt 36-3 strain, (IFO-14037; FERM P-5729; ATCC-31730) induced from the afore-mentioned parent strain *Streptomyces fungicidicus* B-5477 is an example of those employable advantageously.

The enduracidin-excreting ability and m-fluoro-DL-tyrosine-resistance of the microorganisms of this invention serve for increasing the enduracidin-productivity additionally or synergistically, thus the enduracidin-productivity of double mutants having both the properties was found to be several times as high as that of the parent strain.

Such double mutants as above can be induced by a suitable combination of the above-mentioned procedure for obtaining enduracidin-excreting mutants and the above-mentioned procedure for obtaining m-fluoro-DL-tyrosine-resistant mutants.

More concretely stated, at first, enduracidin-excreting mutants are induced from the parent strain, and from the mutants are selectively induced m-fluoro-DL-tyrosine-resistant strains in accordance with the afore-explained procedure. For example, *Streptomyces fungicidicus* Emt 2-140 strain (IFO-14088, FERM P-5730; ATCC-31731) induced from *Streptomyces fungicidicus* GAB-453 strain mentioned hereinbefore is an example which can be used advantageously. On the other hand, into the m-fluoro-DL-tyrosine resistant strain can be endowed with the Enduracidin-excreting ability, to obtain double mutants. Further, these double mutants can be selected from spontaneous mutants.

The microbiological properties of the respective microorganisms thus obtained are, except for enduracidin-excreting ability and/or m-fluoro-DL-tyrosine resistance, are entirely the same as those of the parent strain, *Streptomyces fungicidicus* B-5477 (IFO-12439; ATCC-21013) as described in U.S. Pat. No. 3,786,142 and Journal of Antibiotics, 21, 126 (1968).

For cultivation of these mutants, culture media containing appropriate nutrients, such as assimilable carbon sources, digestible nitrogen sources, inorganic acid salts and/or organic acid salts, which are conventionally employed for cultivation of microorganisms, are used. As the carbon source, there may be employed, for example, carbohydrates such as starch, dextrin, lactose or maltose, or fat and oil such as soybean oil, chicken oil or lard, independently or in combination.

As the nitrogen source, there may be employed, for example, organic or inorganic substances such as corn-gluten-meal, corn-steep-liquor, defatted cotton-seed flour, urea or ammonium sulfate. Inorganic substances such as potassium, sodium, magnesium, zinc, cobalt, iron, manganese, or phosphoric acid are also employed conveniently. As other organic acid salts are employable, for example, potassium or sodium salts of lactic acid, tartaric acid or maleic acid, effectively.

The cultivation is preferably conducted under aerobic conditions, e.g. under shaking or stirring with aeration, usually at a temperature of 20° C.–37° C., the pH being desirably adjusted at 6–9.

Cultivation for 5–9 days under the conditions as above gives enduracidin accumulated in the culture broth at a high potency.

As an example, comparison with the case where the parent strain is used, by employing two kinds of fermentation media as shown in Table 1, is as presented in Table 2.

As is clear from Table 2, enduracidin-excreting mutants are superior to the parent strain in productivity of enduracidin especially in the medium A containing sodium dihydrogen phosphate, and m-fluoro-DL-tyrosine-resistant mutants are superior to the parent strain in enduracidin productivity in the medium B containing no supplemental inorganic phosphate. Further, the double mutants having both properties show 5–8 times as much enduracidin productivity as the parent strain does.

TABLE 1

| Fermentation Media | | |
|---|---|---|
| | Medium A | Medium B |
| Corn flour | 5.0% | 8.0% |
| Corn gluten meal | 4.0 | 3.0 |
| Corn-steep-liquor | 0.5 | 0.5 |
| Sodium dihydrogen phosphate | 2.6 | — |
| Sodium chloride | 0.5 | 0.1 |
| Ammonium sulfate | 0.3 | 0.3 |

TABLE 1-continued

| Fermentation Media | | |
|---|---|---|
| | Medium A | Medium B |
| Zinc chloride | 0.01 | 0.01 |
| Lactose | 1.0 | 1.0 |
| Chicken oil | 1.4 | 1.4 |
| Potassium lactate | 0.1 | 0.5 |
| pH | 6.7 | 6.7 |

TABLE 2

Enduracidin-Productivity of the Parent Strain and its Mutants

| | Amount of Enduracidin Produced* (μg/ml) | |
|---|---|---|
| | Medium A | Medium B |
| Parent Strain (St. fungicidicus B-5477) | 530 | 550 |
| excreting mutant (St. fungicidicus GAB-453) | 1730 | 1240 |
| m-fluoro-DL-tyrosine-resistant mutant (St. fungicidicus Emt 36-3) | 1190 | 2560 |
| excreting and m-fluoro-DL-tyrosine-resistant mutant (St. fungicidicus Emt 2-140) | 2820 | 4340 |

Culture conditions are the same as those in Example 2.
*Determined by the biological assay method discribed just before Example 1-(1)

It has been known that enduracidin produced by the parent strain is accumulated mainly in the mycelium. [The Journal of Antibiotics, 21, 126 (1968)].

Also in case of employing enduracidin-excreting and/or m-fluoro-DL-tyrosine-resistant mutants, a greater part of the enduracidin produced is contained in the mycelium collected by filtration of the culture broth or in the precipitate formed by centrifuge of the culture broth.

It is presumed that, because the free base of enduracidin is hardly soluble in water, the enduracidin excreted out of the mycelia of the mutants is collected by filtration or precipitation together with the mycelia or solid matters in the culture broth. Therefore, recovery of enduracidin produced by these mutants can be conducted by applying various known methods for recovering enduracidin produced by the parent strain. [U.S. Pat. No. 3,786,142; The Journal of Antibiotics, 21, 138 (1968)].

Advantageous processes are, for example, extraction of enduracidin from the filtration residue containing the mycelia with aqueous methanol or acetone acidified with hydrochloric acid, followed by adsorption with activated charcoal, adsorption with synthetic adsorbent resin, ion-exchange with resin, extraction with an organic solvent, salting out, concentration or lyophilization. When enduracidin of a relatively low purity for use of, for example, an additive to feedstuff is desired, it may be sufficient to collect the mycelia by filtration, and to wash them with water and subject them to direct drying with a drier.

The present invention will be further explained by way of the following examples, but these examples should be understood not to limit thereby the present invention. Enduracidin accumulated in the culture broth was subjected to quantitative determination biologically, after, its extraction from the culture broth with 70% acetone acidified with hydrochloric acid, by employing as the test organism *Bacillus subtilis* PCI 219 and using the crystals of enduracidin monohydrochloride (Enduracidin A: Enduracidin B=58:42) as the standard.

EXAMPLE 1-(1)

Agar slant in a test tube containing 8 ml of a medium for sporulation (soluble starch 1.0%, yeast extract 0.2%, powdered agar 2.0%, pH 7.0) was inoculated with *Streptomyces fungicidicus* B-5477 (IFO-12439, ATCC-21013), which was incubated at 28° C. for 10 days to cause sporulation. The spores thus formed were collected by platinum loop, which were suspended in 5 ml of sterile water. In this suspension were contained spores of $5.1 \times 10^8$/ml. The suspension was subjected to filtration by means of the glass-filter No. 2 (40–50 micron). Thus filtered suspension contained spores of $2.6 \times 10^8$/ml. A 4 ml portion of the suspension was transferred a glass-plate (petri dish; 9 cm diameter) and subjected to irradiation of ultra-violet ray (10 W, pasteurizing lamp) at a distance of 40 cm for 10 minutes while shaking the plate, whereby 99.8% of the spores were killed. Thus-treated suspension was diluted with sterile water so as to contain viable spores of 30–50/0.1 ml. This dilution of 0.1 ml was spread on a plate (9 cm diameter) containing 15 ml of agar medium (peptone 0.5%, meat extract 0.5%, sodium chloride 0.5%, powdered agar 2.0%, pH 7.2), which was incubated at 28° C. for four days. On the plate where 30–50 colonies were formed, was layered 5 ml of bouillon-soft-agar medium (agar concentration 0.7%) containing about $1 \times 10^6$/ml of spores of *Bacillus subtilis* PCI 219, which was incubated at 37° C. for 16 hours. Among about 21,000 colonies thus processed, nine colonies formed around them respectively inhibitory zones (15–23 cm diameter) for growth of *Bacillus subtilis* PCI 219. These nine colonies were purified by the use of bouillon agar plate, then transplanted onto the aforementioned slant medium for spore-formation. By the use of this slant culture, a suspension of spores was prepared, which was laid on a bouillon agar plate to cause 10–20 colonies to occur, followed by incubation at 28° C. for four days. On thus incubated medium was layered a bouillon-soft-agar medium containing about the same number of spores of *Bacillus subtilis* PCI 219, which was incubated at 37° C. for 16 hours, then diameter of the formed circular zone where the growth of *Bacillus subtilis* PCI 219 was inhibited was measured. Three of the nine strains did not show the formation of the circular zone, and five of them formed such circular zones as having 15–20 mm diameter. The remaining one strain showed the formation of the largest circular zone (24 mm diameter) where the growth of *Bacillus subtilis* PCI 219 was inhibited. This strain was named *Streptomyces fungicidicus* GAB-453.

EXAMPLE 1-(2)

One-tenth ml each of a spore-suspension ($1.2 \times 10^9$/ml) of *Streptomyces fungicidicus* B-5477 strain (IFO-12439, ATCC-21013), the suspension being prepared by the same procedure as employed in Example 1-(1), was spread on the plate containing 15 ml of the minimal agar medium supplemented with 125 γ/ml of m-fluoro-DL-tyrosine, which was incubated at 28° C. for six days. About 200 colonies were formed per plate. Among them, relatively large sized colonies (about 1.5 mm–2.0 mm, about ten/plate) were streaked on the same minimal medium. Thus streaked media were incubated at 28° C. for five days, then the strains grown on the media were isolated as m-fluoro-DL-tyrosine-resistant ones. Thus-isolated 125 strains were incubated at 28° C. for eight days on the Medium B shown in Table 1, followed by determination of the respective potency. Among them, one strain which showed the highest potency was named *Streptomyces fungicidicus* Emt 36-3.

EXAMPLE 1-(3)

From the *Streptomyces fungicidicus* GAB-453 strain induced by the procedure mentioned in Example 1-(1), a spore-suspension ($2.1 \times 10^9$/ml) was prepared by the same process as in Example 1-(1). Five ml of a bouillon medium containing 200 γ/ml of N-methyl-N'-nitro-N-nitrosoquanidine was inoculated with one ml of the spore-suspension, which was shaken at 28° C. for four hours. By this treatment, about 73% of the spores were killed. Thus-treated suspension was subjected to centrifugal separation at 3,000 rpm. The spores thus precipitated were separated and suspended in 1 ml of sterile water. One-tenth ml of the spore suspension was spread on a plate (diameter 9 cm) containing 15 ml of minimal agar medium supplemented with 60 γ/ml of m-fluoro-DL-tyrosine, which was then incubated at 28° C. for six days. Six days later, the number of colonies reached about 180 per plate. Among them, relatively large sized colonies (about 1.5 mm–2.0 mm, about ten/plate) were streaked on a minimal agar medium of the same composition containing m-fluoro-DL-tyrosine at the concentration of 60 γ/ml. Thus streaked media were incubated at 28° C. for six days. Then, the strains grown on the media were transplanted into agar-slants for sporulation as m-fluoro-DL-tyrosine-resistant strain induced from *Streptomyces fungicidicus* GAB-453 strain. Thus-obtained 75 strains were incubated at 28° C. for eight days in the Medium B shown in Table 1, followed by determination of the respective potencies. Among them, 68 strains showed higher potency than that of the parent strain, *Streptomyces fungicidicus* GAB-453. Among these 68 strains, one strain which showed the highest potency was named *Streptomyces fungicidicus* Emt 2-140. This strain was subjected to the assay in accordance with the procedure shown in Example 1-(1), resulting in formation of growth-inhibition circular zone of *Bacillus subtilis* (24 mm diameter) with no change of enduracidin-excreting ability.

EXAMPLE 2

Twenty ml of a seed-culture medium consisting of corn-steep-liquor (3.5%), corn flour (2.5%), corn gluten meal (0.5%), calcium carbonate (3.0%) and an antifoaming agent Actocol (0.05%), whose pH is 6.2, was pipetted into an Erlenmeyer flask of 200 ml-capacity, which was autoclaved at 120° C. for 15 minutes. Thus-sterilized seed-culture medium was inoculated with one ml of a suspension containing about $2 \times 10^8$ spores of *Streptomyces fungicidicus* Emt-2-140 strain (IFO-14088) induced by the procedure mentioned in Example 1-(3), which was incubated under shaking at 28° C. for 24 hours. Then, 30 ml of the Medium B shown in Table 1 was pipetted into an Erlenmeyer flask of 200 ml-capacity, which was autoclaved at 120° C. for 30 minutes. To this flask was transferred 2.5 ml of the above-mentioned seed-culture, which was incubated under shaking at 28° C. for eight days. Thus-obtained fermentation broth contained 4330 μg/ml of enduracidin. To two liters of this fermentation broth was added 40 g of a filter aid, Hyflo Super Cel, and the mixture was subjected to filtration under suction using a Buchner funnel of 30 cm diameter with filter paper (Toyo Roshi No. 2).

The mycelial fraction thus obtained by filtration was washed with six liters of deionized water, then subjected to filtration. 480 g of thus obtained wet mycelial fraction was made into a slurry with one liter of deionized water, to which was added two liters of methanol. To the mixture was further added 5N HCl, and while the pH was maintained around 3-4, the mixture was stirred at room temperature for three hours, followed by filtration to obtain 2810 ml of extract solution (enduracidin content: 2460 μg/ml). This acidic extract was adjusted to pH 6.0 with 10N NaOH, to which was added 30 g of Hyflo Super Cel, and the resulting amorphous precipitates were removed by filtration. 2700 ml of thus-obtained neutralized extract solution was applied to the column of activated charcoal (500 ml). This column was washed with 500 ml of 60% methanol and one liter of deionized water, followed by elution of enduracidin with a 70% aqueous acetone containing 0.02N HCl. 1.3 l (4610 μg/ml) of thus-obtained fraction dissolving enduracidin was concentrated at a temperature of 45° C. or below under reduced pressure to 500 ml of volume. To the concentrate was added 200 ml of methanol, and the mixture was again concentrated under reduced pressure to 500 ml of volume. This procedure was repeated, followed by removal of acetone by distillation. To 540 ml of thus-obtained concentrate were added 90 ml of water, 1100 ml of methanol and 12.5 g of sodium chloride, followed by adjusting the pH to 7 by the addition of 10N NaOH. The resulting amorphous precipitates were removed by filtration to leave 2530 ml (2173 μg/ml) of the filtrate. This filtrate was passed through a column packed with 700 ml of Amberlite XAD-2 which was previously washed with 4 l of 70% methanol containing 0.01N HCl and 3 l of 50% methanol. The column was washed with 2 l of 50% methanol containing 0.5% of sodium chloride, followed by elution of enduracidin with 50% methanol containing 0.006N HCl. To 650 ml (7530 μg/ml) of thus-obtained fractions containing enduracidin was added 2 g of activated charcoal, and the mixture was stirred for 30 minutes, followed by removal of the activated charcoal by filtration to obtain 620 ml of clear solution. This cleared solution was successively passed through columns of each 90 ml of Amberlite IR-120 (H type) and IR-45 (OH type) to be desalted. These columns were washed with 90 ml each of 50% methanol, and the washings were combined with the desalted solution to obtain 650 ml of the solution. A portion of the solution was diluted with 0.1N HCl, which was subjected to determination of absorbancy. From the absorbancy at 272 nm, the content of enduracidin was calculated as 3.92 g. This solution was adjusted to pH 4.0 with 2N HCl, followed by concentration under reduced pressure to about 120 ml of volume. This concentrate was cooled in an ice bath, and adjusted to pH 9 with 10N NaOH. The free base of the resulting enduracidin was collected by centrifugal separation, which was washed with about 20 ml of cooled 70% aqueous methanol.

The washed enduracidin free base was suspended in 40 ml of methanol and dissolved with adding equimolar of 1N HCl (1.6 ml). Further, the pH was adjusted to 7. This solution was concentrated under reduced pressure to about 15 ml of volume, whereupon white crystals precipitated. The concentrate was left standing at 5° C. for 2 days, followed by collecting the crystals by filtration with glass filter (No. 4). Thus collected wet crystals were suspended in a mixture of 3 ml of water and 26 ml of methanol. The suspension was heated at 50°-55° C. to dissolve. To this solution was added 30 mg of powdered activated charcoal, and the mixture was stirred at 40° C. for 20 minutes, followed by removal of the activated charcoal by filtration with Millipore filter (FH). Thus-obtained filtrate was concentrated under reduced pressure to about 15 ml of volume whereupon the crystals precipitated. The crystals were stored at 5° C. for two days and then collected by filtration with glass filter. The crystals were dried at 50° C. for 15 hours to give about 2.62 g of white prism-like crystals of enduracidin monohydrochloride, m.p. 240°-245° C. (decomp.).

Elementary Analysis (%): Found: C, 52.56±0.5; H, 6.20±0.3, N, 14.70±0.5; Cl, 4.20±0.6.

Optical Rotation: $[\alpha]_D^{23} + 87° \pm 10$, (c=0.5, dimethyl formamide).

Ultraviolet Absorption: $\lambda_{max}^{0.1N\ HCl}$ nm ($E_1\ cm^{1\%}$)=231, (220±10), 272 (123±10).

Enduracidin Content: enduridicin A: enduricidin B=62:38, further contained ca. 1% of enduracidin C and a trace of encuracidin D (by means High-Performance Liquid chromatography).

EXAMPLE 3

500 ml of a seed-culture medium having the same composition as in Example 2 was put into a Sakaguchi flask of 2 l-capacity, which was autocloved at 120° C. for 30 minutes. Thus-sterilized medium was inoculated with 2 ml of a spore-suspension (about $10^9$ spores) of Streptomyces fungicidicus Emt 2-140 strain induced by the procedure disclosed in Example 1-(3). The medium was incubated under shaking at 28° C. for 24 hours. 500 ml of thus-obtained seed culture broth was transferred to a fermenter of 50 l-capacity containing 30 l of a seed-culture medium of the same composition as above, which was incubated at 28° C. for 28 hours under aeration (30 l/min) with stirring (280 r.p.m). Eight liters of thus-incubated seed-culture broth was transferred to a fermenter of 200 l-capacity containing 100 l of the Medium B shown in Table 1, which was incubated at 28° C. for 8 days under aeration (180 l/min) with stirring (180 r.p.m.). Thus-obtained fermentation broth (88 l) contained 4530 μg/ml of enduracidin.

EXAMPLE 4

20 ml of a seed-culture medium, having the same composition as in Example 2, put in an Erlenmeyer flask of 200 ml-capacity was inoculated with 1 ml of a suspension of spores (about $1.5 \times 10^8$) of Streptomyces fungicidicus GAB-453 strain induced by the procedure disclosed in Example 1-(1), which was incubated under shaking at 28° C. for 24 hours. On the other hand, 30 ml of the Medium A shown in Table 1 was pipetted into an Erlenmeyer flask of 200 ml-capacity, which was autoclaved at 120° C. for 30 minutes. To thus-sterilized medium in the flask was transferred to 2.5 ml of the above-mentioned seed culture, which was incubated under shaking at 28° C. for 8 days. Thus-obtained fermentation broth contained 1870 μg/ml of enduracidin.

EXAMPLE 5

20 ml of a seed-culture medium, having the same composition as in Example 2, put in an Erlenmeyer flask of 200 ml-capacity was inoculated with 1 ml of a suspension of spores (about $3 \times 10^8$) of Streptomyces fungicidicus Emt 36-3 strain (IFO-14037) induced by the procedure disclosed in Example 1-(2), which was incubated under shaking at 28° C. for 24 hours. On the other hand, 30 ml of the Medium B shown in Table 1, wherein the concentration of corn-flour was modified into 6.0%, put in an Erlenmeyer flask of 200 ml-capacity, was autoclaved at 120° C. for 30 minutes. To thus-sterilized medium in the flask was transferred to 2.5 ml of the above-mentioned seed-culture, which was incubated under shaking at 28° C. for 8 days. Thus-obtained fermentation broth contained 3100 μg/ml of enduracidin.

EXAMPLE 6

The fermentation broth (2 l) obtained in Example 3 was adjusted to pH 5.5, and then it was heated at 70° C. for 30 minutes. To the fermentation broth was added 40 g of a filter aid, Hyflo Super Cel, and the mixture was subjected to filtration under suction using a Buchner funnel of 30 cm diameter with filter paper (Toyo Roshi No. 2). The mycelial fraction thus obtained was washed with six liters of deionized water. The washed wet mycelial fraction (570 g) thus obtained was dried under reduced pressure at 55° C. for 6 hours, and further dried over phosphorus pentoxide in desiccator at room temperature for 3 days. The resulting dried material was ground in a mortar to obtain 106 g of pale brown dry powder containing mycelia (enduracidin content; 73.4 mg/g).

What is claimed is:

1. A method for producing enduracidin, which comprises cultivating an enduracidin-producing mutant of *Streptomyces fungicidicus* and which has the abilty to excrete or to permeably diffuse enduracidin around colonies thereof on solid medium or has m-fluoro-DL-tyrosine-resistance or has these two properties, until enduracidin is substantially accumulated in the culture broth and then recovering the same.

2. A method according to claim 1, wherein the mutant is cultivated in an aqueous medium containing appropriate nutrients.

3. A method according to claim 1, wherein the mutant has the ability to excrete or to permeably diffuse enduracidin around colonies thereof on solid medium.

4. A method according to claim 3, wherein the mutant is *Streptomyces fungicidicus* GAB-453 (ATCC-31729).

5. A method according to claim 1, wherein the mutant has m-fluoro-DL-tyrosine-resistance.

6. A method according to claim 5, wherein the mutant is *Streptomyces fungicidicus* Emt 36-3 (ATCC-31730).

7. A method according to claim 1, wherein the mutant has both the ability to excrete or to permeably diffuse enduracidin around colonies thereof on solid medium and m-fluoro-DL-tyrosine-resistance.

8. A method according to claim 7, wherein the mutant is *Streptomyces fungicidicus* Emt 2-140 (ATCC-31731).

9. A biologically pure culture of an enduracidin-producing mutant of *Streptomyces fungicidicus* and which has the ability to excrete or to permeably diffuse enduracidin around colonies thereof on solid medium or has m-fluoro-DL-tyrosine-resistance or has these two properties.

10. A culture according to claim 9, wherein the mutant has the identifying characteristics of *Streptomyces fungicidicus* GAB-453 (ATCC-31729).

11. A culture according to claim 9, wherein the mutant has the identifying characteristics of *Streptomyces fungicidicus* Emt 36-3 (ATCC-31730).

12. A culture according to claim 9, wherein the mutant has the identifying characteristics of *Streptomyces fungicidicus* Emt 2-140 (ATCC-31731).

* * * * *